US009251937B2

(12) United States Patent
Bales et al.

(10) Patent No.: US 9,251,937 B2
(45) Date of Patent: Feb. 2, 2016

(54) HEAT STABLE NANOPARTICLE PREPARATIONS AND ASSOCIATED METHODS THEREOF

(75) Inventors: Brian Christopher Bales, Niskayuna, NY (US); Brian James Grimmond, Clifton Park, NY (US); Daniel Eugene Meyer, Clifton Park, NY (US); Bruce Allan Hay, Niskayuna, NY (US); Michael Todd Luttrell, Canton, MI (US)

(73) Assignee: General Electric Company, Niskayuna, NY (US)

( * ) Notice: Subject to any disclaimer, the term of this patent is extended or adjusted under 35 U.S.C. 154(b) by 722 days.

(21) Appl. No.: 13/538,493

(22) Filed: Jun. 29, 2012

(65) Prior Publication Data

US 2014/0003997 A1    Jan. 2, 2014

(51) Int. Cl.
*A61K 49/18* (2006.01)
*H01F 1/00* (2006.01)
*B82Y 5/00* (2011.01)
*B82Y 15/00* (2011.01)
*B82Y 30/00* (2011.01)
*B82Y 40/00* (2011.01)

(52) U.S. Cl.
CPC ............ *H01F 1/0054* (2013.01); *A61K 49/186* (2013.01); *A61K 49/1842* (2013.01); *B82Y 5/00* (2013.01); *B82Y 15/00* (2013.01); *B82Y 30/00* (2013.01); *B82Y 40/00* (2013.01)

(58) Field of Classification Search
CPC ............ H01F 1/0054; A61K 49/1824; A61K 49/183; A61K 49/1842; A61L 2/04; A61L 2/06; A61L 2/08; B82Y 5/00; B82Y 15/00; B82Y 30/00; B82Y 40/00
See application file for complete search history.

(56) References Cited

U.S. PATENT DOCUMENTS

| 5,314,679 A | 5/1994 | Lewis et al. |
| 5,352,459 A | 10/1994 | Hollister et al. |
| 6,267,989 B1 | 7/2001 | Liversidge et al. |

(Continued)

FOREIGN PATENT DOCUMENTS

| EP | 0605024 A2 | 7/1994 |
| GB | 2472446 A | 2/2011 |

(Continued)

OTHER PUBLICATIONS

Rucareanu, Simona et al. "Polymer-capped gold nanoparticles by ligand-exchange reactions." Journal of Materials Chemistry (2008) 18 5830-5834.*
Search Report and Written Opinion from corresponding PCT Application No. PCT/EP2013/063456 dated Sep. 18, 2013.
Ting-Jung et al., "Targeted folic acid-PEG nanoparticles for noninvasive imaging of folate receptor by MRI", Journal of Biomedical Materials Research Part A, vol. 87A, No. 1, pp. 165-175, Oct. 1, 2008.

*Primary Examiner* — Timothy Cleveland
(74) *Attorney, Agent, or Firm* — Paul J. DiConza

(57) ABSTRACT

A method of sterilizing a nanoparticle preparation at a high temperature is provided. A plurality of nanoparticles are purified to form the preparation, wherein the nanoparticles comprise at least a core and a shell and the shell comprises one or more ligand species attached to the core. The nanoparticle preparation is made by a purified nanoparticle composition, a carrier fluid and an excess of the one or more ligand species not attached to the core. The ligand species attached to the core and the excess ligand species added after purification are structurally identical. The nanoparticle preparation provided by the present invention may be used as contrast agents in medical imaging techniques such as X-ray and magnetic resonance imaging.

7 Claims, 2 Drawing Sheets

(56) References Cited

U.S. PATENT DOCUMENTS

2011/0104072 A1* 5/2011 Bales et al. ............ 424/9.32
2011/0165647 A1 7/2011 Fernig et al.
2012/0156142 A1 6/2012 Hay et al.

FOREIGN PATENT DOCUMENTS

| WO | 2009098510 A2 | 8/2009 |
| WO | 2011051422 A2 | 5/2011 |
| WO | 2012080290 A1 | 6/2012 |

* cited by examiner

HEAT STABLE NANOPARTICLE PREPARATIONS AND ASSOCIATED METHODS THEREOF

FIELD

This invention relates generally to methods for stabilizing a nanoparticle preparation. Such nanoparticle preparations are useful for a variety of therapeutic and diagnostic applications.

BACKGROUND

Nanoparticles, i.e. particles whose diameters are appropriately measured in nanometers, have been considered for a wide variety of end uses. Nanoparticles with appropriate imaging properties are typically based on transition metal oxides, and used as contrast agents for MR and/or X-ray imaging. Iron oxide nanoparticles are used in various therapeutic applications such as iron replacement therapy, magnetic particle imaging (MPI), drug targeting or gene delivery. Preparations containing nanoparticle compositions to be used for in vivo applications in human individuals are typically required to be purified and sterilized to prevent biological contamination, and are often desired to exhibit robust suspension stability in isotonic aqueous media.

Various methods for sterilization of nanoparticles exist, including UV irradiation, ethylene oxide treatment, formaldehyde treatment, sterile filtration, gamma irradiation, and autoclave sterilization. The autoclave sterilization for injectable contrast agents is considered to be one of the most reliable and inexpensive sterilization techniques.

Nanoparticle compositions in aqueous suspension are often subject to agglomeration and precipitation during the use of heat sterilization techniques, such as autoclaving. Efforts have been made to modify the surface properties of such nanoparticles to enhance the stability of aqueous suspensions of such nanoparticles by adding various surface modifiers. Use of a cloud point modifier to alter the temperature at which the nanoparticle aggregation occurs, enabling sterilization via autoclave, is an alternate approach. However, in some cases the cloud point modifiers are charged molecules and are different than the molecules which constitute the shell of the nanoparticles, and that introduces a risk of modifying the surface chemistry of the shell as well as the composition of the nanoparticles.

Methods for stabilizing a nanoparticle composition at elevated temperatures during autoclave sterilization without altering the nanoparticle surface chemistry are highly desirable. A preparation of the nanoparticle composition including improved stability, sterility, enhanced safety, and resistant to aggregation during heat sterilization, is advantageous for various applications.

BRIEF DESCRIPTION

One or more embodiments of a method comprise purifying a composition to form a purified composition, wherein the purified composition comprises at least one nanoparticle disposed in a carrier fluid, the nanoparticle comprising a core and a shell attached to the core, the shell comprising a ligand species, adding a quantity of the ligand species to the purified composition to form a preparation, wherein at least a portion of the added quantity of the ligand species remains unattached to the core, and sterilizing the preparation.

Another embodiment of a method comprises purifying a composition to form a purified composition, wherein the purified composition comprises at least one nanoparticle disposed in a carrier fluid, the nanoparticle comprising a core and a shell attached to the core, the shell comprising a ligand species and wherein the purified composition is devoid of any excess ligand species; adding a quantity of the ligand species to the purified composition to form a preparation, wherein at least a portion of the added quantity of the ligand species remains unattached to the core and sterilizing the preparation by autoclaving.

BRIEF DESCRIPTION OF THE DRAWING

These and other features, aspects, and advantages of the present invention will become better understood when the following detailed description is read with reference to the accompanying drawings in which like characters represent like parts throughout the drawings, wherein.

DETAILED DESCRIPTION

Figure 1:
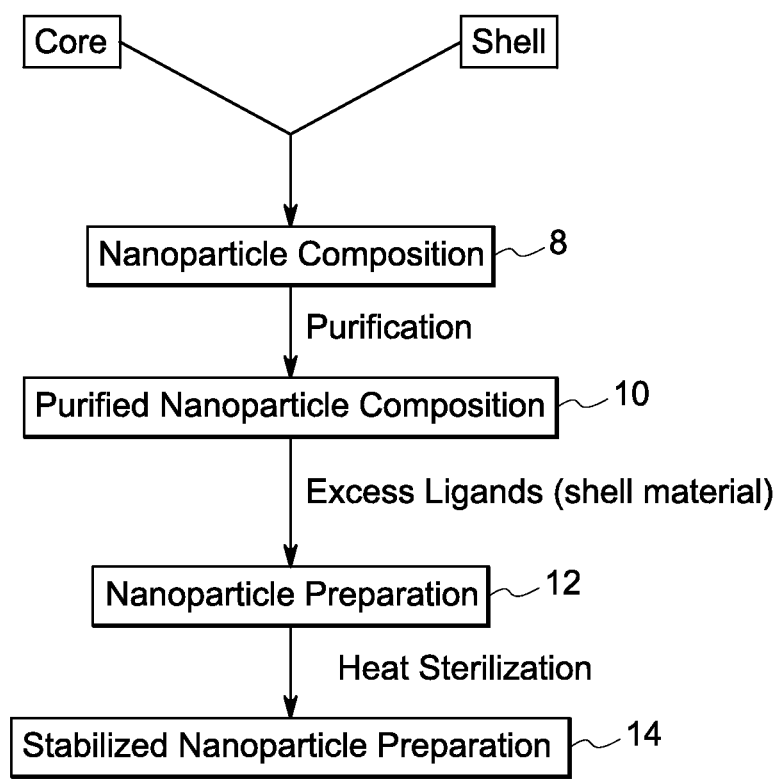
FIG. 1 is a flow chart depicting an exemplary method of making a stabilized nanoparticle preparation, in accordance with one embodiment of the present invention.

In the following specification and the claims which follow, reference will be made to a number of terms, which shall be defined to have the following meanings.

The singular forms "a", "an" and "the" include plural references unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

Embodiments of the present invention comprise a method comprising purifying a composition to form a purified composition, wherein the purified composition comprises at least one nanoparticle disposed in a carrier fluid, the nanoparticle comprising a core and a shell attached to the core, the shell comprising a ligand species. The purification is followed by adding a quantity of the ligand species to the purified composition to form a preparation, wherein at least a portion of the added quantity of the ligand species remains unattached to the core. The preparation is then subjected to sterilization.

More specifically, in one or more embodiments, a method comprises providing at least one nanoparticle comprising at least a core and a shell and the shell comprises a ligand species attached to the core. The nanoparticle composition is purified to form a purified nanoparticle composition, and a preparation is formed using the purified nanoparticle composition by adding a quantity of the ligand species, which addition may help to stabilize the preparation during autoclave sterilization at high temperature. The purification is performed to eliminate undesirable extraneous species present in the composition including, for instance, excess starting material or any impurities. The purification incidentally removes any excess ligand species, that is, ligand species not attached to the nanoparticle cores, present in the nanoparticle composition. In one example, the purification of nanoparticles may employ filtration based on molecular weight cut off, wherein the pore size of the filter membrane limits the molecules of a particular molecular weight to pass through the pores. In another example, the purification of nanoparticles may employ washing by centrifugation followed by re-suspension in a carrier fluid. Because of size difference of ligand species and nanoparticle composition (core-shell), the purification facilitates the removal of excess ligand species from the nanoparticle composition. An excess of the ligand species is added to a purified nanoparticle composition to form a preparation followed by sterilization. The sterilization of the preparation produces a sterilized preparation.

As noted, the preparation comprises a purified nanoparticle composition. In some embodiments, the nanoparticle composition comprises at least a core and a shell. The shell comprises a ligand species, wherein the ligand species is attached to the core. A ligand species that is attached to the core may be referred to herein as "bound ligand species".

In one embodiment, the nanoparticle composition comprises a core-shell structure, wherein the core comprises a transition metal, such as a core comprising a transition metal oxide. Specific examples include oxides of tungsten, tantalum, hafnium, zirconium, zinc, molybdenum, silver, iron, manganese, copper, cobalt, nickel or combinations of two or more of the foregoing transition metal oxides. In one embodiment, the core comprises a super paramagnetic iron oxide. In one or more embodiments, metal content of the plurality of nanoparticles in the preparation is in a range of 0.5 to 300 mg/mL. The structure and composition of the core is described in greater detail hereinafter, more specifically with reference to FIG. 2.

In one or more embodiments, the nanoparticle shell comprises a ligand species comprising a structural moiety, wherein the structural moiety comprises an organic phosphate or phosphonate and one or more hydrophilic groups. In one embodiment, the ligand species comprises at least one phosphate or phosphonate group and one or more additional groups comprising polyethylene ether moieties, polypropylene ether moieties, polybutylene ether moieties or combinations of two or more of the foregoing moieties. In some embodiments, the nanoparticle shell comprises a ligand species comprising at least one phosphate group or phosphonate group and one or more hydrophilic groups comprising polyethylene ether moieties. In some embodiments, the shell comprises one or more ligand species, wherein the ligand species comprises a phosphate, a phosphonate or a combination thereof. The phosphate may comprise a monophosphate, a bis(phosphate), a polyphosphate or a combination thereof. The phosphonate may comprise an alpha-hydroxy phosphonate, a mono-phosphonate, a bis-phosphonate, a polyphosphonate, or a combination thereof. In some other embodiments, the ligand species further comprise a poly(ethylene glycol) (PEG) functional group. In some embodiments, the shell comprises poly(ethylene glycol) (PEG) functionalized phosphates, PEG functionalized monophosphates, PEG functionalized α-hydroxy phosphonates, PEG functionalized bis(phosphates) or combinations thereof. PEG is a hydrophilic polymer, and the shell made of PEG functionalized ligand species largely enhances the surface hydration, thus enhancing solubility and in vivo compatibility of the particles. The structure and composition of the shell is described in greater detail hereinafter, more specifically with reference to FIG. 2.

In one or more embodiments, the method includes adding a quantity of ligand species to the purified composition to form a preparation that includes an excess of ligand species not attached to the core. The ligand species added to the purified nanoparticle composition for making the preparation is structurally identical to the ligand species present in the shell which are attached to the nanoparticle core. As noted, the term "at least a portion of the added quantity of the ligand species remains unattached to the core" is interchangeably used herein as "free ligand species" or "excess free ligand species". The free ligand species are also structurally identical with the ligand species bound to the nanoparticle core.

At elevated temperature, the bound ligand species may dissociate from the core, which enhances the probability of aggregation of the nanoparticles. The aggregation of the nanoparticles may be reduced in presence of the free ligand species in the preparation. Without being bound by theory, it is suggested that the ligand species dissociated from the core may be replaced by the free ligand species, wherein the mechanism is referred to herein as a "ligand exchange". The presence of free ligand species in the preparation maintains the integrity of the core-shell structure of the nanoparticles, even at elevated temperature.

In one or more embodiments, the free ligand species present in the preparation may replace the dissociated ligand species from the core, and as the free and bound ligand species are structurally identical, the surface chemistry of the nanoparticles remains unchanged. In one or more embodiments, the free ligand species comprises poly(ethylene glycol) (PEG) functionalized monophosphates, PEG functionalized alpha-hydroxy phosphonates, PEG functionalized bis (phosphates) or combinations thereof. In one example, if the bound ligand species of a nanoparticle composition is PEG functionalized alpha-hydroxy phosphonate, the free ligand species present in the preparation is also PEG functionalized alpha-hydroxy phosphonate, which maintains the surface properties of the nanoparticle during sterilization. The concentration of the free ligand species changes with a change in concentration of the nanoparticles in the preparation. In one or more embodiments, the quantity of the free ligand species added to the preparation is in a range of about 0.005 to 2 moles of ligand relative to the moles of metal present in the nanoparticle core.

As noted, the preparation further comprises a carrier fluid. In one or more embodiments, the carrier fluid comprises water, ethanol, or combinations thereof. The core-shell structure of the nanoparticle remains stabilized, that is, suspended without undue aggregation in the carrier fluid. In one or more embodiments, the addition of additional compounds to the carrier fluid may increase the ionic strength of the nanoparticle preparation. In one or more embodiments, the additional compounds comprise saccharides such as mannitol, dextrose, sucrose, lactose, sorbitol, xylitol, and maltitol; alcohols such as propylene glycol; synthetic polymers such as unmodified PEGs, and polyvinylpyrrolidinone; surfactants such as Tweens, Cremaphors, and Labasols; and any physiologically compatible salts (e.g., sodium chloride, sodium bromide, sodium sulphate, sodium acetate, sodium bicarbonate, potassium chloride, potassium bromide, potassium sulphate, potassium acetate, potassium bicarbonate) or combinations thereof. In some embodiments, the carrier fluid may be used to make the nanoparticle suspension. In one example, ethanol is used as a carrier fluid, wherein the ethanol may be evaporated at the last step of making the preparation to form an aqueous suspension of nanoparticles. In one or more embodiments, the carrier fluid may be used as a diluent. The carrier fluid may also be used to optimize or modify the concentration of the nanoparticles or excess ligand species in the preparation. In some embodiments, where the preparation is used as a contrast agent, the carrier fluid is used in an injectable medium comprising the nanoparticle preparation. In one or more embodiments, the carrier fluid may function as a pharmaceutical excipient. When the preparation is used as a pharmaceutical drug carrier, the fluid may be used as a medium for the drug carrier.

In some embodiments, the method further comprises adding a quantity of fluid to the carrier fluid. The quantity of fluid is added to the composition to adjust the concentration of the metal within a specified range. The added quantity of fluid may comprise ethanol, water or combination thereof. In some other embodiments, the method further comprises adding a quantity of pharmaceutically acceptable excipients, such as buffers, sugars, salts or combination of two or more excipients. For example, the pharmaceutically acceptable salts comprise sodium chloride, sodium bromide, sodium sulphate, sodium acetate, sodium bicarbonate, potassium chloride, potassium bromide, potassium sulphate, potassium acetate, potassium bicarbonate. For some other examples, the pharmaceutically acceptable sugars may comprise mannitol, dextrose, sucrose, lactose, sorbitol, xylitol, and maltitol.

As noted, in some embodiments, the preparation is sterilized by heat sterilization, wherein the heat sterilization can be categorized as dry heat sterilization and moist heat sterilization. In a specific embodiment, the preparation is heat sterilized by autoclaving.

In one or more embodiments of the method, the preparation is sterilized by autoclaving at high temperature. The autoclave sterilization may be performed in compliance with regulations for standard autoclave sterilization methods. The term "high temperature" or "elevated temperature" may be referred to herein as a temperature which is suitable for autoclaving, such as more than 100° C. In heat sterilization, the sterilization depends on incubation temperature and the incubation time. The bacteria, viruses, fungi, or spores may be destroyed by autoclaving at the typical 134° C. for at least 3 minutes or 121° C. for at least 15 minutes. In one or more embodiments of the steam or moist heat sterilization, the nanoparticle preparation is sterilized at temperature of about 121° C. for a time period of at least about 15 minutes. In some embodiments, the condition of 121° C. for a time period of about 15 minutes is attained by using steam at a pressure of 15 pounds per square inch (psi) in excess of atmospheric pressure, at altitudes near sea level. The dry heat sterilization may also be performed, although the temperatures used for dry heat sterilization are typically 160° C. for 1 to 2 hours. In one or more embodiments of the method, the preparation is sterilized by autoclaving. In some embodiments, for autoclaving, the temperature is maintained at 121° C. for 15 minutes. In some other embodiments, the preparation is sterilized at a temperature of about 256° C. for at least 5 minutes.

Unlike other heat sterilization processes where nanoparticles typically form aggregates, the nanoparticles are resistant to aggregation during heat sterilization in embodiments of the present invention. In one or more embodiments, the method may prevent aggregation of the nanoparticles due to an exchange of one or more of the excess free ligand species with the one or more ligand species attached to the core during sterilization. The ligand species form a shell around the core of the nanoparticles to stabilize the core.

As noted, the method comprises providing a composition comprising at least one nanoparticle comprising a core and a shell attached to the core. The composition is then purified to form a purified composition comprising at least one nanoparticle disposed in a carrier fluid. A quantity of the ligand species is also added to the purified composition to form a preparation followed by sterilization of the preparation. An exemplary embodiment of the method that provides a stabilized nanoparticle preparation is described in greater detail with reference to FIG. 1.

Particularly, FIG. 1 illustrates a flow chart depicting an exemplary method for making stabilized nanoparticle preparations that are stable at high temperature. A plurality of core-shell nanoparticles 8 form by combining at least a core and a shell. In general, the method for making a nanoparticle composition comprises contacting a nanoparticulate metal oxide core with a shell composition of the present invention, wherein the shell comprises a ligand species comprising an organic phosphate or phosphonate and one or more hydrophilic groups. Typically, the contact is carried out in a mixture comprising at least one organic solvent and water. The purification of nanoparticles generates purified core-shell nanoparticles 10 eliminating any extraneous species present in the core shell precursors, any excess ligand species after ligand species exchange to form core-shell nanoparticles or other materials non-specifically bound to the particles. In one or more examples, the nanoparticles are purified by filtration based on molecular weight cut off principle, followed by washing via centrifugation and subsequent re-suspension of the purified nanoparticles in a carrier fluid. An excess of ligand species of the same shell material and a carrier fluid are added to the purified nanoparticles to form a nanoparticle preparation, 12. The preparation 12 is then subjected to, for example, heat sterilization.

In some embodiments of the method, the stabilized preparation may have equilibrium between the ligand species bound to the nanoparticle core and the free ligand species. At room temperature, the nanoparticle composition may be in equilibrium such that the vast majority of the bound ligand species (shell molecules) interact with the nanoparticle core, providing a well coated core/shell structure and preventing nanoparticle aggregation.

As noted, in some embodiments during sterilization at higher temperature, the bound ligand species dissociate from the core, which may destabilize the nanoparticle's core-shell structure and increase the probability of aggregation. The bound ligand species may be in an equilibrium state with the water molecules of the aqueous suspension of the nanoparticles. The expected rate of ligand species exchange with water molecules or with other ligand species may be faster at higher temperature. Based on a theoretical estimation, the bound ligand species may dissociate from the core at a faster rate at high temperature and the water molecules may substitute the dissociated ligand species in absence of the excess free ligand species. The nanoparticles with insufficient shell coverage may form aggregates. Based on another theoretical assumption, the addition of excess ligand species to the preparation may adjust the equilibrium in such a way so that the ligand species bound to the core maintain the integrity of the core-shell structure at elevated temperatures. In one assumption, the addition of the ligand species as free ligand species to the purified composition of core-shell nanoparticles during autoclave sterilization (typically 121° C.) results in greater increase of the ratio of unbound ligand species to bound ligand species and helps to ensure that the ligand species bound to the core maintain the integrity of the core-shell structure at elevated temperatures.

Figure 2:
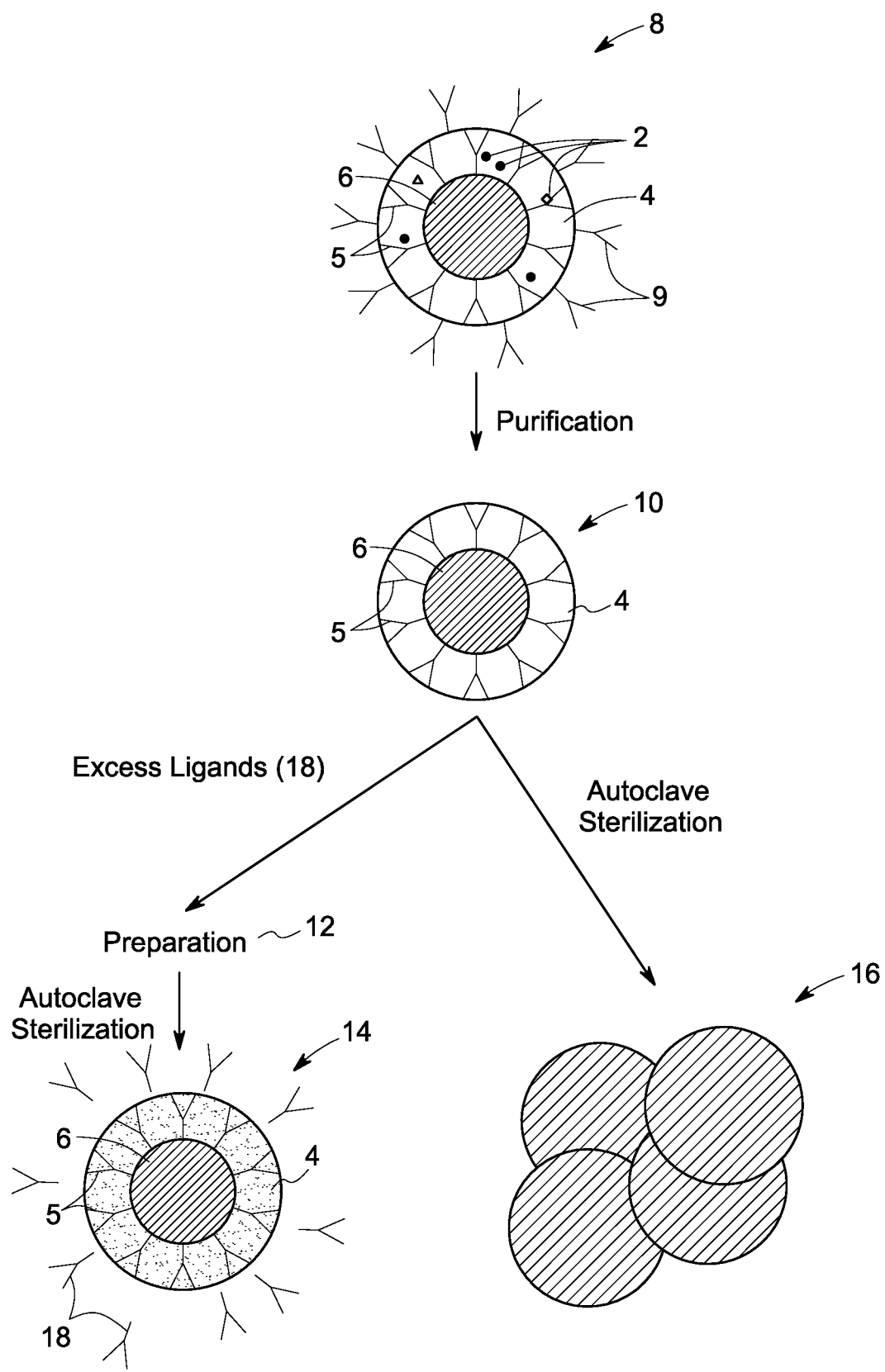
FIG. 2 is a schematic flow diagram depicting an exemplary method of making a stabilized nanoparticle preparation, including configurations of the idealized cross sectional view of the core-shell nanoparticles, in accordance with one embodiment of the present invention.

Referring to FIG. 2, an exemplary method illustrates formation of stabilized nanoparticle preparations during autoclave sterilization, wherein the idealized cross sectional views of the nanoparticles comprising core-shell structure are depicted herein. FIG. 2 illustrates in detail, a schematic representation of a series of steps employed in an exemplary method, wherein the plurality of core-shell nanoparticles 8 form by combining at least a core 6 and a shell 4. The shell 4 comprises ligand species 5 attached to the core 6. The nanoparticle 8 comprises excess ligand species 9 and other impurities 2 which are removed by purification, resulting in formation of a purified nanoparticle composition 10. The nanoparticle composition comprises at least one nanoparticle disposed in a carrier fluid. After purification, the nanoparticles may be subjected to autoclave sterilization with or without adding a quantity of ligand species which are same as the shell material. If the purified nanoparticle composition 10 is subjected to autoclave sterilization in absence of the added quantity of ligand species, aggregation of the nanoparticles 16 may occur. Another path illustrates a quantity of ligand species 18 added to the purified composition 10 to form a nanoparticle preparation 12, wherein the added quantity of the ligand species is structurally identical to the ligand species of the shell material. The preparation 12 is then subjected to autoclave sterilization to form a stabilized nanoparticle preparation 14, wherein the preparation 14 is resistant to aggregation at a higher temperature during autoclaving.

The core-shell nanoparticles may be made with standard procedures known in the art. The core-shell nanoparticle suspension is washed to remove the excess ligand species or other impurities nonspecifically attached to the nanoparticles, followed by concentrating the nanoparticle suspension for further use. The purified nanoparticle composition is then used to make a preparation comprising the purified nanoparticle composition, excess ligand species which are structurally identical as the shell material, and a carrier fluid. The preparation is then subjected to autoclave sterilization. The Experimental Section of this disclosure provides further guidance on the preparation of the nanoparticle composition provided by the present invention.

One or more embodiments of the invention are related to a nanoparticle composition 10 having an idealized core-shell structure shown in FIG. 2. The nanoparticle composition 10 comprises a nanoparticulate metal oxide core 6, and a shell 4 as described in FIG. 2. In one embodiment, the present invention provides a nanoparticle composition characterized by its ability to form an aqueous suspension that exhibits substantial stability towards heat sterilization at high temperature.

As noted, the preparation comprises constituent nanoparticles, the shape and size of the nanoparticles may vary depending on the method of making the nanoparticles. The cross-sectional geometries of the nanoparticles may be different, which include but are not limited to a sphere, a rod, a tube, a flake, a fiber, a plate, a wire, a cube, and a whisker. In one embodiment, a cross-sectional geometry of the particle may be one or more of circular, ellipsoidal, triangular, rectangular, polygonal or irregular shape. Non-spherical nanoparticles alternatively may have the shape of cones or elongated rods. In one embodiment, the nanoparticles are spherical in shape.

Typically the nanoparticles have an average particle size of less than 1 micrometer. As used herein, the term 'size' refers to the hydrodynamic diameter ($D_H$) of the nanoparticles as measured by dynamic light scattering. In one embodiment, the nanoparticle composition provided by the present invention has a $D_H$ in a range from about 2 nm to about 500 nm. In an alternate embodiment, the nanoparticle composition provided by the present invention has a $D_H$ in a range from about 10 nm to 25 nm. In one embodiment, the nanoparticle composition provided by the present invention has a $D_H$ of less than 50 nm. In another embodiment, the nanoparticle composition provided by the present invention has a $D_H$ of less than 10 nm. In yet another embodiment, the nanoparticle composition provided by the present invention has a $D_H$ of less than 5 nm. A small particle size may be advantageous in, for example, facilitating clearance of the nanoparticle composition from the kidneys and other organs of a subject following a medical imaging procedure employing the nanoparticle composition as a contrast agent.

In one or more embodiments, the preparation may comprise nanoparticles in various forms, such as crystalline form or amorphous form. In one embodiment, the nanoparticles present in the preparation are in crystalline form. In some alternate embodiments, the nanoparticles of the preparation are present in the amorphous form. In some embodiments, the preparation may comprise nanoparticles as a mixture of both crystalline and amorphous forms.

In one embodiment, the preparation comprises a mixture of nanoparticles, wherein the distribution of the nanoparticles is homogeneous. For example, the preparation may comprise a single type of nanoparticles, wherein the shape and size of each of the nanoparticles are about the same. In an alternate embodiment, the preparation comprises a mixture of nanoparticles, wherein the distribution of the nanoparticles is non-homogeneous. In some other embodiments, the preparation may comprise a mixture of different types of nanoparticles, wherein the size of the nanoparticles or shape of the nanoparticles may be different.

The relatively easy dispersion of the nanoparticles in the preparation may prevent agglomeration and/or aggregation at room temperature. An aggregate may include more than one nanoparticle in physical contact with one another, while agglomerates may include more than one aggregate in physical contact with one another.

The metal oxide core of the nanoparticle composition has dimensions appropriately measured in nanometers. In various embodiments, the nanoparticulate metal oxide core may be prepared as a suspension in a diluent and the hydrodynamic diameter of the suspended nanoparticulate metal oxide core particles may be measured, for example by dynamic light scattering. In one embodiment, the size of the nanoparticulate metal oxide core is measured by Transmission Electron Microscopy (TEM). The diameter of the nanoparticulate metal oxide core is in a range from about 1 nm to about 100 nm. In an alternate embodiment, the nanoparticulate metal oxide core has a diameter of about 1 to 30 nm. In one or more embodiments, the nanoparticulate metal oxide core comprises a nanoparticulate super paramagnetic iron oxide (SPIO) and has a diameter as measured by TEM of less than about 25 nm.

In one embodiment, the core comprises a transition metal. In certain embodiments, the core comprises one or more derivatives of transition metal elements, such as oxides, carbides, sulfides, nitrides, phosphides, borides, halides, selenides and tellurides that contain one or more of these transition metal elements. The term "metal" signifies the presence of a metallic or nonmetallic material that contains a transition metal element as a constituent.

As noted earlier, in one embodiment, the nanoparticulate metal oxide core comprises a transition metal oxide comprising oxides of tungsten, tantalum, hafnium, zirconium, zinc, molybdenum, silver, iron, manganese, copper, cobalt, nickel or combinations of two or more of the foregoing transition metal oxides. In some embodiments, the metal oxide core comprises a transition metal, which exhibits magnetic behavior, including, for example, super paramagnetic behavior. In some embodiments, the metal oxide core comprises a paramagnetic metal, selected from the group consisting of iron, manganese, copper, cobalt, nickel or combinations thereof. In a specific embodiment, the metal oxide core comprises super paramagnetic iron oxide (SPIO). In one embodiment, the iron oxide is doped with another metal. In one or more embodiments, the core of the nanoparticle comprises super paramagnetic iron oxide and the nanoparticle has a particle size up to about 50 nm.

In one embodiment, the nanoparticulate metal oxide core consists of a single transition metal oxide, for example tantalum oxide, hafnium oxide, or iron oxide alone. In another embodiment, the nanoparticulate metal oxide core comprises two or more transition metal oxides. Thus in one embodiment the nanoparticulate metal oxide core comprises both tantalum oxide and hafnium oxide, or tantalum oxide and iron oxide. In one embodiment, the nanoparticulate metal oxide core comprises only iron oxide.

Typically, the nanoparticulate metal oxide core comprises at least 30% by weight of the transition metal component of the transition metal oxide. Relatively high transition metal content in the nanoparticulate metal oxide core may provide nanoparticle compositions with a relatively higher degree of radiopacity per unit volume, thereby imparting more efficient performance as a contrast agent. The relatively high transition metal content potentially gives the particles utility as contrast agents in X-ray imaging applications, such as computed tomography (CT). Examples of transition metal elements that may provide this property include tungsten, tantalum, hafnium, zirconium, molybdenum, silver, and zinc.

In some embodiments, the nanoparticle preparation of the present invention may be used as magnetic resonance (MR) contrast agents. For use as MR contrast agents, the nanoparticle composition provided by the present invention advantageously comprises a paramagnetic metal species, with those compositions that comprise a superparamagnetic metal species being of particular interest. Examples of potential paramagnetic and superparamagnetic materials include materials comprising one or more of iron, manganese, copper, cobalt, nickel or zinc. A particularly interesting group of materials are those based upon iron oxide, especially SPIO's, which typically comprise from about 65% to about 75% iron by weight for the core. In one embodiment, the nanoparticulate metal oxide core comprises an iron compound having general formula $[Fe_2^+O_3]_x[Fe_2^+O_3(M^{2+}O)]_{1-x}$ wherein $1 \geq x \geq 0$ and $M^{2+}$ is a metal cation such as cations of iron, manganese, nickel, cobalt, magnesium, copper, zinc and a combination of such cations. Examples of iron compounds falling within the scope of this general formula include magnetite ($Fe_3O_4$) when the metal cation ($M^{2+}$) is ferrous ion ($Fe^{2+}$) and $x=0$; and maghemite ($\gamma$-$Fe_2O_3$) when $x=1$.

The nanoparticle composition 10 comprises a shell 4 which completely covers the nanoparticulate metal oxide core 6, as shown in FIG. 2. Thus, in certain embodiments, the nanoparticle composition is said to comprise a shell which substantially covers the core. The term "substantially covers" means that a percentage surface coverage of the core by the shell is greater than about 20% while compared to a core without a shell on it. As used herein, the term "percentage surface coverage" refers to the ratio of the core surface covered by the shell to the core surface not covered by the shell. In some embodiments, the percentage surface coverage of the nanoparticle may be greater than about 40%.

In some embodiments, the shell 4 may facilitate improved water solubility, reduce aggregate formation, prevent oxidation of nanoparticles, maintain the uniformity of the core-shell entity, and/or provide biocompatibility for the nanoparticle compositions.

The average thickness of shell 4 is typically in a range from about 1 to about 50 nm. In one embodiment, the shell has an average thickness less than 50 nm. In another embodiment, the shell has an average thickness of less than 8 nm. In yet another embodiment, the shell has an average thickness of less than 5 nm.

In one or more embodiments, the nanoparticle compositions may comprise more than one shell layer disposed on the nanoparticulate metal oxide core. By judicious selection of processing conditions, a nanoparticulate metal oxide core species may be prepared as a suspension in a diluent and thereafter treated under a first set of conditions with one or more stabilizer substances to generate a first nanoparticle composition comprising a first shell, and thereafter the first nanoparticle composition is treated under a second set of conditions with one or more different stabilizer substances which generate a second nanoparticle composition comprising both the first shell and a second shell.

Nanoparticle compositions provided by the present invention are not meant to suggest a 1:1 stoichiometry between the nanoparticulate metal oxide core and the shell comprising ligand species, but rather to identify the nanoparticle composition as comprising a nanoparticulate metal oxide core and shell comprising ligand species. The ligand species comprises at least one structural moiety comprising organic phosphate or phosphonate groups comprising one or more hydrophilic groups. As noted, the organic phosphate or phosphonate comprising one or more hydrophilic groups may be in a fully protonated form, or in an ionized form. Typically, a plurality of organic phosphate or phosphonate comprising one or more hydrophilic groups may be associated with the surface of a given nanoparticulate metal oxide core particle. In some embodiments, the ligand species is bound to the nanoparticulate metal oxide core via hydrogen bonds. In some embodiments, the ligand species is bound to the nanoparticulate metal oxide core via at least one covalent bond. In other embodiments, the ligand species may be bound to the nanoparticulate metal oxide core via ionic bonds.

As noted, the nanoparticles comprise a ligand species comprising an organic phosphate or phosphonate and one or more hydrophilic groups. The hydrophilic group (or groups) is selected from the polyethylene ether moieties. Polyethylene ether moieties are defined as moieties comprising oxyethyleneoxy structural units —$OCH_2CH_2O$—, and/or substituted oxyethyleneoxy structural units. For convenience and because of the close structural association with the term polyethylene glycol (PEG), such moieties may at times herein be referred to as PEG groups, or PEG moieties, and are characterized by a moiety molecular weight. Similarly, polypropylene ether moieties are defined as moieties comprising oxypropyleneoxy structural units —$OCH_2CH_2CH_2O$— and/or substituted oxypropyleneoxy structural units. For convenience, polypropylene ether moieties may be referred to at times herein as polypropylene glycol groups or moieties. Similarly, polybutylene ether moieties are defined as moieties comprising oxybutyleneoxy structural units —$OCH_2CH_2CH_2CH_2O$— and/or substituted oxybutyleneoxy structural units. For convenience polybuylene ether moieties may at times herein is referred to as poly-THF moieties.

In some embodiments, the shell comprises a ligand species comprising one phosphate group, alternatively stated herein as monophosphate. In one or more embodiments, the phosphate is attached to PEG moiety, wherein the molecular weight of PEG may be 350, 440, 750, 2000 or 5000 daltons. Accordingly, the ligand species are referred to herein as mPP350, wherein mPP350 represents monophosphate linked with PEG 350. More specifically, mPP350 is defined as a PEG molecule with molecular weight ~350 g/m, with one terminal hydroxyl group methoxylated and the other terminal hydroxyl group converted to a phosphate monoester. Similarly, mPP440, mPP750, mPP2000 or mPP5000 may also be used for nanoparticle preparations.

In embodiments where the shell comprises a ligand species comprising at least two phosphate groups, the two phosphate groups may occupy positions which constitute a 1,2; 1,3; 1,4; 1,5; or 1,6 spatial relationship to one another. A 1,2 spatial relationship of the at least two phosphate groups includes embodiments which are 1,2-bisphosphates; 2,3-bisphosphates; 3,4-bisphosphates; 4,5-bisphosphates, 5,6-bisphosphates and so on. Those of ordinary skill in the art will fully understand the extension of this principle to 1,3; 1,4; 1,5; and 1,6 spatial relationships of the at least two phosphate groups. As used herein, the nanoparticle compositions comprising such ligands, the designation "1,2-BPP350" refers to a structural moiety comprising two phosphate groups configured in a 1,2 spatial relationship and a polyethylene ether moiety having a moiety molecular weight of 350 daltons. Similarly, the designation "1,2-BPP440" refers to a ligand species comprising two phosphate groups configured in a 1,2 spatial relationship and a polyethylene ether moiety having moiety molecular weight of 440 daltons.

In one or more embodiments, the shell comprises a ligand species, wherein the ligand species comprising a mono phosphonate, bis phosphonate or α-hydroxyphosphonate. In one embodiment, the nanoparticle shell comprises a phosphonate and PEG as a hydrophilic moiety, which results in a ligand species that is a PEG functionalized phosphonate. In some embodiments, the nanoparticle shell comprises α-hydroxyphosphonate and a hydrophilic moiety which is linked via a carbon atom carrying the α-hydroxy group. In one or more embodiments, the α-hydroxyphosphonate is attached to PEG moiety, wherein PEG molecular weight may be 350, 440, 750, 2000, 5000, 10000 or 30000 daltons. Accordingly, the ligand species are referred to herein as α-HmPP350, wherein α-HmPP350 represents α-hydroxyphosphonate linked with PEG 350. Similarly, α-HmPP440, α-HmPP750, α-HmPP2000, α-HmPP5000, α-HmPP10000 or α-HmPP30000 may also be used for nanoparticle preparations. Nanoparticles considered for use in in vivo treatment for human subjects, the linkage between the α-hydroxyphosphonate and a hydrophilic moiety may be a hydrocarbon, which minimizes the probability of any interaction between such treated nanoparticles and human tissue.

As noted, the ligand species comprises one or more hydrophilic groups comprising polyethylene ether moieties. The effectiveness of the ligand species in stabilizing the nanoparticulate metal oxide core (and the nanoparticle composition as a whole) has been found to depend upon its structure. In various embodiments, the effectiveness of the ligand species in stabilizing the nanoparticulate metal oxide core is dependent upon the size of the hydrophilic moiety which may at times herein be described in terms of the group molecular weight of the hydrophilic group.

In general, the structure of the ligand species may be tailored to be effective in stabilizing a particular nanoparticulate metal oxide core, and the hydrophilic group present in the ligand species may have either a relatively low group molecular weight (e.g. less than 100 grams per "mole") or a relatively high group molecular weight (e.g. more than 10,000 grams per "mole"). As the hydrophilic group comprises one or more of polyethylene ether moieties, the size and molecular weights of these moieties, at times herein referred to as moiety molecular weight, contribute to the group molecular weight of the hydrophilic group as a whole. In one embodiment, the hydrophilic group comprises a polyethylene ether moiety having a moiety molecular weight in a range from about 750 daltons to about 20,000 daltons. In an alternate embodiment, the hydrophilic group comprises a polyethylene ether moiety having a moiety molecular weight of about 2000 daltons. In yet another embodiment, the hydrophilic group comprises a polyethylene ether moiety having a moiety molecular weight of less than 20,000 daltons. In yet still another embodiment, the hydrophilic group comprises a polyethylene ether moiety having a moiety molecular weight of less than 2000 daltons. In yet another embodiment, the hydrophilic group comprises a polyethylene ether moiety having a moiety molecular weight of less than 350 daltons. As used herein, "daltons" and "grams per mole" may be used as interchangeable terms which when applied either to the group molecular weight of a hydrophilic group or the moiety molecular weight of a polyethylene ether moiety and substituted variants of such moiety, and expresses the weight in grams of that group or moiety present in a mole of the ligand species which contains it.

In one or more embodiments, the ligand species of the nanoparticle composition may, in certain embodiments, comprise a hydrophilic group containing groups in addition to the ether linkages (—O—) found in polyalkylene ether moieties. Thus, a wide variety of functional groups in addition to ether groups may be present in the ligand species, for example ester groups, amine groups, amide groups, carbamate groups, urea groups, carbonate groups, thioether groups, selenoether groups, siloxane groups, sulfinyl groups, sulfonyl groups, and combinations of two or more of the foregoing groups. In some embodiments, such functional groups may be constituents of the hydrophilic group itself or may constitute a part of the ligand species which is not identified as the hydrophilic group. The intended end use of the nanoparticle compositions may impact the choice of such functional groups.

The intended end use of the nanoparticle composition may impact the selection of the hydrophilic groups used in the ligand species. For instance, where the nanoparticle compositions are to be used in vivo, particularly in human subjects, it may be desirable to avoid hydrophilic groups which might bind strongly to tissue components such as proteins. For in vivo use, hydrophilic groups with essentially no net charge, such as polyalkylene ethers are of particular interest. In addition, for use in human subjects, hydrophilic groups that permit the nanoparticle composition to be easily and reproducibly characterized for safety evaluation are particularly desirable. The nanoparticle composition provided by the present invention typically has a zeta potential in a range from about −40 mV and +40 mV.

As noted, the nanoparticle composition provided by the present invention typically comprises a transition metal oxide core and a shell comprised of a ligand species disposed in a carrier fluid. In the nanoparticle composition, the ratio of the shell to the core may be determined by elemental analysis. From knowledge of the chemical make up of the metal oxide nanoparticles and their average size before treatment with the ligand species, a calculation can be made of the amount of the ligand species per nanoparticulate metal oxide core particle. In one embodiment, the present invention provides a nanoparticle composition comprising a nanoparticulate iron oxide core and a shell comprising a ligand species, wherein the molar ratio of the ligand species to iron is in a range from about 0.01 to about 0.25.

As noted, the nanoparticle compositions provided by the present invention may be used as contrast agents for diagnostic imaging. In such an application, these nanoparticle compositions are administered to a subject, in some embodiments a mammalian subject, and then the subject is thereafter subjected to imaging. The nanoparticle compositions provided by the present invention may be particularly useful in MR imaging though they may also find utility as contrast agents in ultrasound or radioactive tracer imaging. In addition, the nanoparticle compositions provided by the present invention may be useful in other areas such as cell culture infusion. In some embodiments, the nanoparticles comprise one or more therapeutic agents or diagnostic agents. In some embodiments, the sterilized preparations are used as a contrast agent, or for therapeutic applications; examples include magnetic resonance imaging (MRI), drug delivery, gene delivery, replacement therapy or other.

In one embodiment, the present invention provides a diagnostic agent composition which may be delivered to the site of administration as a stable aqueous colloidal suspension with the proper osmolality and pH, as a concentrated aqueous colloidal suspension suitable for dilution prior to administration to a subject. In an alternate embodiment, the present invention provides a diagnostic agent composition as a powder, such as obtained by lyophilization, suitable for reconstitution.

In one embodiment, the present invention provides a sterilized preparation, which may be used as a diagnostic agent composition suitable for injection into a mammalian subject. The diagnostic agent composition comprises a nanoparticle preparation of the present invention and a pharmaceutically acceptable carrier or excipient. In one embodiment, the excipient is an optional component of the diagnostic agent composition. Suitable excipients are illustrated by, but not limited to, one or more of salts, disintegrators, binders, fillers, and lubricants. In one embodiment, the pharmaceutically acceptable carrier may be substantially water.

Diagnostic agent compositions provided by the present invention may be prepared by contacting a nanoparticle composition of the present invention with a pharmaceutically acceptable carrier and/or excipient.

When used in diagnostic imaging, particularly of mammalian subjects and more particularly of human subjects, the diagnostic agent compositions provided by the present invention are typically administered as a suspension in a pharmaceutically acceptable carrier which may (but is not required to) comprise one or more excipients. If the administration is to be by injection, particularly parenteral injection, the carrier is typically an aqueous medium that has been rendered isotonic by the addition of about 150 mM of NaCl, 5% dextrose, mannitol or combinations thereof. It typically also has an appropriate (physiological) pH of between about 7.3 and 7.4. The administration may be intravascular (IM), subcutaneous (SQ) or most commonly intravenous (IV). However, the administration may also be via implantation of a depot that then slowly releases the nanoparticles into the subject's blood or tissue. Alternatively, the administration may be by ingestion for imaging of the GI tract or by inhalation for imaging of the lungs and airways.

The administration to human subjects, particularly intravenous administration, requires that the diagnostic agent composition may be non-toxic in the amounts used and free of any infective agents such as bacteria and viruses and also free of any pyrogens. Thus, the nanoparticle composition present in the diagnostic agent composition should be stable to the necessary purification procedures and not suffer degradation in their hydrophilicity or change in the size of the constituent nanoparticles.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

EXPERIMENTAL SECTION

The core-shell nanoparticles were synthesized and purified using the procedures known in the art. The excess ligand species were synthesized for producing a preparation of the invention and used in following examples. Manufacture of such ligand species and core-shell nanopartciles can be found in Patent Application Publication No. US 20110104072A1 and patent application Ser. No. 12/968,645. A typical method of synthesizing a ligand species, such as α-hydroxy PEG-350 mono(methyl ether) phosphonate is described herein. Examples for the synthesis of PEG350 with alpha-hydroxy phosphonate, PEG5000 with alpha-hydroxy phosphonate, PEG5000 with bis phosphonate and the synthesis of purified SPIO coated with PEG5000 with alpha-hydroxy phosphonate are described herein.

Example 1

Synthesis of Excess Ligand Species, Such as PEG350 Alpha Hydroxy Phosphonate

Synthesis of a PEG-350 Conjugate

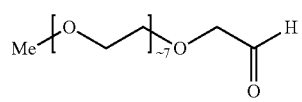

Synthesis of PEG-350 mono(methyl ether) acetaldehyde: To a solution containing PEG-350 mono(methyl ether) (3.438 g, 9.82 mmol) dissolved in $CH_2Cl_2$ (98 mL) was added Dess-Martin Periodinane (5.00 g, 11.79 mmol) and the resulting solution was stirred at room temperature for 20 h. During the reaction a fine, white precipitate was formed and was removed at the end of the reaction via filtration through a celite pad. The solvent was removed from the filtrate in vacuo to leave a white solid suspended in a yellow oil. The solid was triturated with diethyl ether, and the solid was removed by filtration through a celite pad. Removal of the solvent from the filtrate in vacuo left the product PEG-350 mono(methyl ether) acetaldehyde (3.42 g, 100%) as a yellow oil. $^1$H NMR ($CDCl_3$) δ 9.73 (t, J=4 Hz, 1H), 4.16 (d, J=4 Hz, 2H), 3.65 (m, 24H), 3.38 (s, 3H) ppm. IR (neat) 2873, 1732, 1455, 1350, 1109, 1040, 948, 851, 749 $cm^{-1}$.

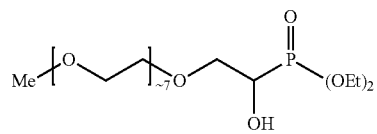

Synthesis of diethyl α-hydroxy PEG-350 mono(methyl ether) phosphonate: To a solution containing PEG-350 mono (methyl ether) acetaldehyde (3.71 g, 10.7 mmol) dissolved in tetrahydrofuran (53 mL) was added diethyl phosphite (1.77 g, 12.8 mmol). The solution was cooled to 0° C., and 1,8- diazabicyclo[5.4.0]undec-7-ene (1.94 g, 12.8 mmol). After stirring at 0° C. for 10 min, the reaction was warmed to room temperature and stirred for an additional 24 h. The solvent was removed in vacuo to leave a dark yellow oil which was purified via column chromatography (100% $CH_2Cl_2$ to 15% MeOH/85% $CH_2Cl_2$) to give 3.30 g (64%) of the desired diethyl α-hydroxy PEG-350 mono(methyl ether) phosphonate product as a yellow oil. $^1$H NMR ($CDCl_3$) δ 4.19 (m, 6H), 3.65 (m, 24H), 3.38 (s, 3H), 1.34 (m, 6H) ppm. $^{31}$P NMR ($CDCl_3$) δ 23.1 ppm. IR (neat) 3343, 2872, 1725, 1453, 1248, 1105, 965, 850, 791 $cm^{-1}$.

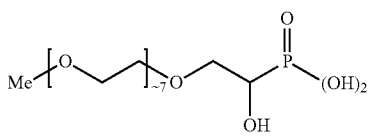

Synthesis of α-hydroxy PEG-350 mono(methyl ether) phosphonic acid: To a solution containing diethyl α-hydroxy PEG-350 mono(methyl ether) phosphonate (3.61 g, 7.43 mmol) dissolved in methylene chloride (74 mL) was added trimethylsilyl bromide (3.41 g, 22.3 mmol) and the resulting solution was stirred at room temperature for 2 h. The solvent was removed in vacuo to leave a brown oil. The resulting oil was dissolved in acetone (74 mL) and water (0.5 mL) and the resulting solution was stirred at room temperature for 1.5 h. The solvent was then removed in vacuo to leave the desired α-hydroxy PEG-350 mono(methyl ether) phosphonic acid product (2.66 g, 84%) as a golden oil. $^1$H NMR ($CDCl_3$) δ 3.65 (m, 24H), 3.38 (s, 3H). $^{31}$P NMR ($CDCl_3$) δ 24.0 ppm. IR (neat) 3460, 2870, 1727, 1456, 1351, 945, 849 $cm^{-1}$.

Example 2

Synthesis of Excess Ligand Species, Such as PEG5000 Alpha Hydroxy Phosphonate

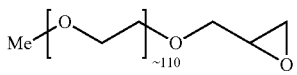

Synthesis of mPEG5000-epoxide: Water (4.32 mL) was suspended in epichlorohydrin (84.68 mL, 1.080 mol) and NaOH (43.20 g, 1.080 mmol) was added followed by triethylammonium hydrochloride (1.18 g, 0.009 mol). The solution was stirred and heated to 70° C. during which time PEG5000 mono(methyl ether) (500 g, 0.100 mol) was added in portions as the temperature rose. The resulting suspension was stirred at temp for 4 h and then cooled to rt. Water (500 mL) was added and the product was extracted with $CH_2Cl_2$ (2×1000 mL). The $CH_2Cl_2$ was removed in vacuo (not to dryness—but only to a thick oil) and the resulting oil was recrystallized from THF (400 mL)/hexanes (200 mL) (add THF, heat and then add hexanes, swirl until cloudiness clears ~30 s) to give 499.93 g (99% of theoretical mass) of the desired product as an off white solid: $^1$H NMR ($CDCl_3$) δ 3.81 (m, 2H), 3.64 (m, 422H), 3.46 (m, 2H), 3.38 (s, 3H), 3.17 (m, 1H), 2.79 (m, 1H), 2.61 (m, 1H). $^{13}$C NMR ($CDCl_3$) δ 71.97, 71.89, 70.53, 59.00, 50.76, 44.22.

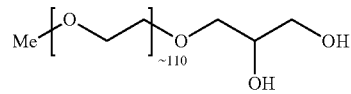

Synthesis of mPEG5000-diol: mPEG5000-epoxide (499.93 g, 98.88 mmol) was dissolved in 0.5 M $H_2SO_4$ (2000 mL) and stirred at room temperature for 1.5 h (~30 min to fully dissolve material and the 1 additional hour reaction). The reaction was then extracted with $CH_2Cl_2$ (2×1000 mL). The $CH_2Cl_2$ was removed in vacuo (not to dryness—but only to a thick oil) and the resulting oil was recrystallized from THF/hexanes (400 mL:200 mL) (add THF, heat and then add hexanes, swirl until cloudiness clears ~30 s) to give 411.88 g (82% of theoretical mass) of the desired product as an off white solid: $^1$H NMR ($CDCl_3$) δ 3.75 (m, 2H), 3.57 (m, 422H), 3.39 (m, 2H), 3.31 (s, 3H). $^{13}$C NMR ($CDCl_3$) δ 72.88, 71.91, 70.55, 63.93, 59.02.

Synthesis of mPEG5000-aldehyde: mPEG5000-diol (208 g, 40.99 mmol) was dissolved in water (320 mL) and stirred at room temperature for ~45 min. To this cloudy solution was added a pre-dissolved solution of $NaIO_4$ (10.7 g, 50 mmol) in water (90 mL) was added in equal portions over ~30 min. The cloudiness cleared after ~1.5-2 h following the final oxidant addition. The reaction was then stirred for 16 h and quenched by the addition of propylene glycol (1.20 mL). The aqueous reaction mixture was then extracted with $CH_2Cl_2$ (1×1000 mL, 1×500 mL). The organic layers were combined, and the $CH_2Cl_2$ was removed in vacuo (not to dryness —but only to a thick oil). The resulting golden oil was recrystallized from THF/hexanes (400 mL:200 mL) (add THF, heat and then add hexanes, swirl until cloudiness clears ~30 s) to yield 183.77 g (89% of theoretical mass) of the desired product as a white solid: $^1$H NMR ($CDCl_3$) δ 9.66 (m, 1H), 4.10 (m, 2H), 3.75 (m, 2H), 3.58 (m, 422H), 3.39 (m, 2H), 3.31 (s, 3H). $^{13}$C NMR ($CDCl_3$) δ 200.94, 71.90, 71.18, 70.54, 59.01, 53.56.

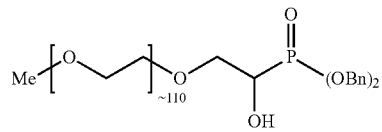

Synthesis of dibenzyl-αHmPP5000: mPEG5000-aldehyde (181.453 g, 35.97 mmol) was dissolved in $CH_2Cl_2$ (850 mL) and triethylamine (5.01 mL, 35.97 mmol) was added and allowed to stir for ~30 min. This was followed by a slow addition of dibenzyl phosphite (9.43 g, 35.97 mmol). After stirring at room temperature for 48 h, the solvent was removed in vacuo (not to dryness—but only to a thick oil) and the resulting oil was recrystallized from THF/hexanes (350 mL:175 mL) (add THF, heat and then add hexanes, swirl until cloudiness clears ~30 s) to give 175.59 g (92% of theoretical mass) of the desired product as a white solid: $^1$H NMR ($CDCl_3$) δ 7.34 (m, 10H), 5.10 (m, 4H), 3.79 (m, 1H), 3.75 (m, 2H), 3.64 (m, 460H), 3.53 (m, 4H), 3.37 (s, 3H). $^{13}$C NMR ($CDCl_3$) δ 136.40, 136.27, 128.74, 128.60, 128.43, 127.99, 71.98, 71.17, 70.61, 68.67, 68.13, 64.85, 67.59, 59.08. $^{31}$P NMR (CDCl$_3$) δ 23.92.

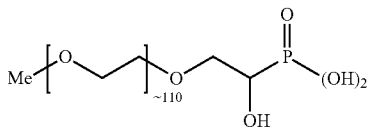

Synthesis of αHmPP5000: Dry dibenzyl-αHmPP5000 (122.80 g, 23.15 mmol) was suspended in absolute ethanol (500 mL) and water (25 mL) and 10% Pd on carbon (4.0 g) was slowly added. The reaction was then stirred under an atmosphere of H2 (balloon pressure) until uptake was complete. The Pd on carbon was removed via filtration through a celite pad, and the solvent was removed from the filtrate in vacuo (not to dryness—but only to a thick oil). The resulting oil was recrystallized from THF/hexanes (300 mL:150 mL) to give 109.7 g (94% of theoretical mass) of the desired product as a white powder: $^1$H NMR (CDCl$_3$) δ 3.81 (m, 4H), 3.64 (m, 366H), 3.47 (m, 2H), 3.38 (s, 3H) ppm. $^{13}$C NMR (CDCl$_3$) δ 72.00, 71.04, 70.54, 59.11 ppm. $^{31}$P NMR (CDCl$_3$) δ 22.85 ppm.

Example 4

Synthesis of PEG5k Bis Phosphate (BPP5000)

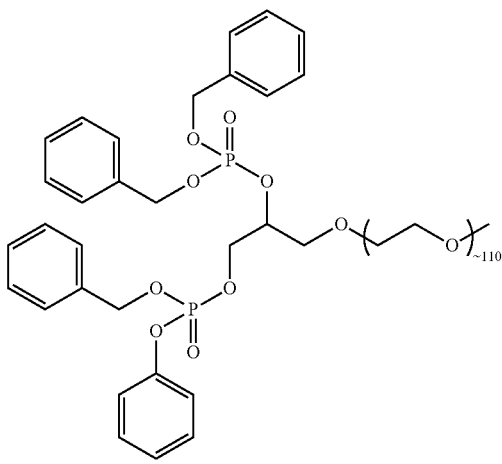

Synthesis of mPEG5000-1,2-bis(bibenyzl phosphate): Dibenzyl N,N-diisopropylphosphoramidite (16.34 g, 97.3 mmol) was dissolved in CH$_2$Cl$_2$ (600 mL). Tetrazole (0.45M in acetonitrile, 47.3 mmol) was added and the resulting solution was stirred at room temperature for 30 min mPEG5000-diol (60.0 g, 11.8 mmol) dissolved in CH$_2$Cl$_2$ (100 mL) was then added and the resulting solution was stirred at 50° C. for 48 h. The reaction was then cooled to room temperature and t-butylhydroperoxide (4.26 g, 47.3 mmol) was added to the reaction mixture. The reaction was stirred at room temperature for 4.5 h and was then washed with a 10% (w./v.) solution of sodium sulfite (200 mL). The resulting aqueous layer was then extracted with CH$_2$Cl$_2$ (500 mL). The organic layers were combined, and the solvent was removed in vacuo to give an off white solid which was purified via column chromatography (100% CH$_2$Cl$_2$ to 20% MeOH/80% CH$_2$Cl$_2$) on silica gel to give 47.47 g (72%) of the desired product as a white solid. $^1$H NMR (CDCl$_3$) δ 7.31 (m, 20H), 5.04 (m, 8H), 4.63 (m, 1H), 4.14 (m, 2H), 3.74 (m, 3H), 3.65 (m, 440H), 3.38 (s, 3H) ppm. $^{31}$P NMR (CDCl$_3$) δ 0.03, −0.75 ppm.

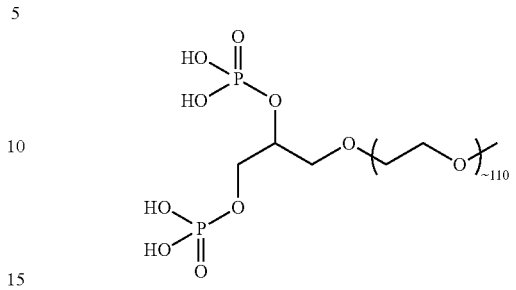

Synthesis of PEG5k bis phosphate (BPP5000): mPEG5000-1,2-bis(bibenyzl phosphate) (46.46 g, 8.33 mmol) was dissolved in ethanol (300 mL). 10% Pd on carbon (2 g) was then added and the resulting suspension was stirred under H$_2$ (1 atm) for 48 h. The catalyst was removed by filtration through a celite pad and removal of the solvent from the filtrate left a clear oil. The oil was crystallized from 2:1 THF/hexanes (300 mL). The crystals were collected via vacuum filtration and washed with hexanes (2×50 mL) to give 40.4 g (74%) of the desired product as a white solid. $^1$H NMR (CDCl$_3$) δ 4.71 (m, 1H), 4.20 (m, 2H), 3.65 (m, 440H), 3.38 (s, 3H) ppm. $^{13}$C NMR (CDCl$_3$) δ 74.90, 71.70, 70.34, 65.86, 58.81 ppm. $^{31}$P NMR (CDCl$_3$) δ 1.18, 0.53 ppm.

Example 5

Synthesis of Purified SPIO Nanoparticles Coated with PEG5000 Alpha-Hydroxy Phosphonate (aHmPP5000)

9.177 g αHmPP5000 ligand species was weighed into a 1 L Erlenmeyer flask containing a magnetic stir bar. 8.955 ml of NaOH solution (0.2 M) was added along with 104 ml deionized water and absolute EtOH (200 mL). The flask was covered with a watch glass and stirred with magnetic stirring and gentle heating until a clear colorless solution was obtained. The above solution was added to 2 L jacketed reactor with mechanical stirrer, Teflon anchor agitator, thermocouple, nitrogen inlet and bubbler, and a reflux condenser. The flask was rinsed with absolute EtOH (2×25 mL), and the rinse was added to the reactor. The clear, colorless solution was stirred at 100 rpm. 330.6 ml of iron oxide nanoparticle core solution in benzyl alcohol (6.05 g Fe/ml) was added to the reaction mixture via a base washed, DI water rinsed, oven dried graduated cylinder through the powder funnel. The graduated cylinder was rinsed with absolute EtOH (2×25 mL) and the rinse was added to the reactor. A single phase, dark red-brown solution was observed. The stirring rate was increased to 200 rpm and the reactor was stoppered and heated under nitrogen with stirring for 18 h at 50° C. (internal temperature). After heating for 18 h, the reactor was cooled to 25° C. EtOAc (660 mL) and deionized water (320 mL) were added to the reactor and baffles were inserted for enhanced mixing. The reaction mixture was stirred at 500 rpm for 10 min. Stirring was stopped and the phases were allowed to separate. The cloudy mixture began to phase separate in <10 min and a clean phase split was observed after ~30 min. The lower aqueous phase (containing the SPIO particles), consisting of 247 grams of dark red-brown solution, was drained from the reactor into a 2 L 24/40 round bottomed flask. The solution was diluted with water to 800 mL (theory ~2.5 mg Fe/mL) and rotary evaporated briefly to remove any residual volatile organics. The solution was then sterile filtered (0.22 μm) and purified by tangential flow filtration (TFF) using a 50 kDa PES Millipore 0.1 m² membrane. The product was washed with 24 L of deionized water over ~3 hr @ ~10 psi while maintaining a 2.5 L volume in the retentate reservoir. Once the washing was complete, the retentate was concentrated to ~120 grams (~16 mg Fe/mL). The final particles had a hydrodynamic diameter of 19.2 nm as measured in a 150 mM sodium chloride solution by dynamic light scattering.

Example 6

Autoclave Sterilization with Excess Ligand Species

Ligand species, as the mono-sodium salt (0.01 to 0.25 molar equivalents vs. Fe), was dissolved in an aqueous solution containing ligand species coated SPIO nanoparticles. Additional water was added to give a solution with a final iron concentration of 1-30 mg Fe/mL. The resulting solution was autoclaved in a sealed glass container using a Tuttnauer 2340EA or a Steris SV-148H autoclave for 15 min at 121° C.

Example 7

Autoclave Sterilization with Excess Ligand Species and Other Additives

Ligand species, as the mono-sodium salt (0.01 to 0.25 molar eq vs. Fe), was dissolved in an aqueous solution containing ligand species coated SPIO nanoparticles. Additional water and other additives (EtOH; 10% by final volume or d-mannitol; 5% by final volume) were added to give a solution with a final iron concentration of 1-30 mg Fe/mL. The resulting solution was autoclaved in a sealed glass container using a Tuttnauer 2340EA or a Steris SV-148H autoclave for 15 min at 121° C.

Example 8

Autoclave Sterilization without Excess Ligand Species

A ligand species coated SPIO nanoparticle was diluted with additional water to give a solution with a final iron concentration of 1-30 mg Fe/mL. The resulting solution was autoclaved in a sealed glass container using a Tuttnauer 2340EA or a Steris SV-148H autoclave for 15 min at 121° C.

Example 9

Autoclave Sterilization with Other Additives and without Excess Ligand Species

An aqueous solution containing ligand species coated SPIO nanoparticles was diluted with additional water and other additives (EtOH; 10% by final volume or D-mannitol; 5% by final volume) to give a solution with a final iron concentration of 1-30 mg Fe/mL. The resulting solution was autoclaved in a sealed glass container using a Tuttnauer 2340EA or a Steris SV-148H autoclave for 15 min at 121° C.

Example 10

General Procedure for SPIO Nanoparticle Size Measurement by Dynamic Light Scattering An aliquot of the SPIO solution (pre or post autoclave) was diluted to between 0.1 and 0.3 mg Fe/mL in 150 mM aqueous NaCl. The resulting solution was passed through a Whatman Anotop 10 0.2 μm syringe filter and the filtrate was collected in a dust free polystyrene DLS cuvette. The size was measured using a Brookhaven Instruments Inc. ZetaPALS instrument fitted with a 90° light scattering detector and the effective diameter was reported.

The data presented in table 1 shows the size of the SPIO nanoparticles before and after autoclave sterilization in presence and absence of excess ligand species. SPIO nanoparticles comprising alpha hydroxyl monophosphate ligand species, such as aHmPP350, aHmPP750, aHmPP2000, aHmPP5000 and aHmPP30000 illustrates almost same size before and after the autoclave sterilization in presence of excess ligand species and additives. Such as the size of each of the nanoparticles is 10.9, 11.2, 15.3, 20.8 and 29.2 nm respectively after autoclave sterilization in presence of excess ligand species, whereas the nanoparticles form aggregate with diameter greater than 200 nm in absence of excess ligand species in all these preparations.

The SPIO nanoparticles with mPP2000 and mPP5000 also show similar aggregation profile in absence of any additives. Similarly, the SPIO nanoparticles comprising monophosphate ligand species, such as mPP2000 illustrates almost same size of about 23.5 and 24 nm before and after the autoclave sterilization respectively in presence of excess ligand species and in absence of any additives, whereas the nanoparticles form aggregate with diameter greater than 200 nm in absence of excess ligand species in the preparation.

Similar observation was also found for the SPIO nanoparticles comprising bisphosphate ligand species, such as BPP5000 which illustrates almost same size of about 26.4 and 26.6 nm before and after the autoclave sterilization respectively in presence of excess ligand species and ethanol additives, whereas the nanoparticles form a particle with diameter of about 47.8 nm which is greater than a single nanoparticle composition in absence of excess ligand species in the preparation.

TABLE 1

Aggregation of nanoparticles on autoclaving without using excess ligand species

| Ligand species | Equivalent excess ligand species vs. Fe | [Fe] (mg/mL) | Additional additive | Size pre autoclave (nm) | Size post autoclave (nm) |
|---|---|---|---|---|---|
| aHmPP350 | 0.25 | 2.0 | 5% D-mannitol | 9.4 | 10.9 |
| aHmPP350 | 0 | 2.0 | 5% D-mannitol | 9.4 | >200ᵃ |
| aHmPP750 | 0.25 | 10.0 | 5% D-mannitol | 10.4 | 11.2 |
| aHmPP750 | 0 | 10.0 | 5% D-mannitol | 10.4 | >200ᵃ |
| aHmPP2000 | 0.25 | 10.0 | 5% D-mannitol | 13.7 | 15.3 |
| aHmPP2000 | 0 | 10.0 | 5% D-mannitol | 13.7 | >200ᵃ |
| aHmPP2000 | 0.125 | 20.0 | None | 17.0 | 16.9 |
| aHmPP2000 | 0 | 20.0 | None | 15.3 | >200ᵃ |
| aHmPP5000 | .25 | 10.0 | 5% D-mannitol | 20.6 | 20.8 |
| aHmPP5000 | 0 | 20.0 | None | 15.9 | >200ᵃ |
| aHmPP5000 | 0.125 | 20.0 | None | 19.4 | 24.1 |
| aHmPP5000 | 0.01 | 30.0 | 10% ethanol | 20.6 | 22.6 |
| aHmPP30000 | 0.01 | 2.0 | 10% ethanol | 28.5 | 29.2 |

TABLE 1-continued

Aggregation of nanoparticles on autoclaving without using excess ligand species

| Ligand species | Equivalent excess ligand species vs. Fe | [Fe] (mg/mL) | Additional additive | Size pre autoclave (nm) | Size post autoclave (nm) |
|---|---|---|---|---|---|
| aHmPP30000 | 0 | 2.0 | 10% ethanol | 28.5 | >200[a] |
| mPP2000 | 0.25 | 1.0 | None | 23.5 | 24.2 |
| mPP2000 | 0 | 1.0 | None | 23.5 | >200[a] |
| BPP5000 | 0.01 | 30.0 | 10% ethanol | 26.4 | 26.6 |
| BPP5000 | 0 | 27.0 | 10% ethanol | 25.2 | 47.8 |

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method comprising the steps of:
    (a) purifying a composition to form a purified composition, wherein the purified composition comprises at least one nanoparticle disposed in a carrier fluid, the nanoparticle comprising a core and a shell attached to the core, the shell comprising a ligand species,
    (b) adding a quantity of the ligand species to the purified composition to form a preparation, wherein at least a portion of the added quantity of the ligand species remains unattached to the core; and
    (c) sterilizing the preparation by autoclaving;
    wherein the core comprises an oxide of a paramagnetic metal comprising iron; and the ligand species comprises PEG functionalized alpha-hydroxy phosphonate.

2. The method of claim 1, wherein the core comprising the oxide of the paramagnetic metal comprising iron is a super paramagnetic iron oxide.

3. The method of claim 1, wherein the at least one nanoparticle has a hydrodynamic diameter in a range of about 1 nm to 100 nm.

4. The method of claim 1, wherein the carrier fluid comprises water, ethanol or combination thereof.

5. The method of claim 1 further comprising adding a quantity of fluid to the carrier fluid, wherein the fluid comprises ethanol, water or combination thereof.

6. The method of claim 1 further comprising adding one or more compounds comprising mannitol, dextrose, propylene glycol, a physiologically compatible salt or combinations thereof.

7. The method of claim 1, further comprising adding one or more pharmaceutically acceptable excipients to the carrier fluid, wherein the pharmaceutically acceptable excipients comprises a pharmaceutically acceptable salt, a pharmaceutically acceptable sugar moiety or a combination thereof.

* * * * *